United States Patent [19]

Lins

[11] Patent Number: 5,167,950
[45] Date of Patent: Dec. 1, 1992

[54] HIGH ALCOHOL CONTENT AEROSOL ANTIMICROBIAL MOUSSE

[75] Inventor: Claudio L. K. Lins, Racine County, Wis.

[73] Assignee: S. C. Johnson & Son

[21] Appl. No.: 676,917

[22] Filed: Mar. 28, 1991

[51] Int. Cl.$^5$ .............................................. A61K 9/14
[52] U.S. Cl. ...................................... 424/47; 424/71; 514/873
[58] Field of Search .................. 424/71, 47; 252/90, 252/132; 514/873

[56] References Cited

U.S. PATENT DOCUMENTS

| | | | |
|---|---|---|---|
| 2,054,989 | 9/1936 | Moore | 167/58 |
| 3,131,152 | 4/1964 | Klausner | 252/305 |
| 3,131,153 | 4/1964 | Klausner | 252/305 |
| 3,282,776 | 11/1966 | Kitzke et al. | 167/39 |
| 3,395,214 | 7/1968 | Mummert | 424/47 |
| 3,395,215 | 7/1968 | Schubert | 424/47 |
| 3,770,648 | 11/1973 | Mackles | 252/305 |
| 3,824,303 | 7/1974 | Lanzet et al. | 424/47 |
| 3,840,465 | 10/1974 | Knowles et al. | 252/90 |
| 3,922,977 | 12/1975 | Lavo et al. | 111/1 |
| 3,962,150 | 6/1976 | Viola | 252/542 |
| 4,145,411 | 3/1979 | Mende | 424/45 |
| 4,224,319 | 9/1980 | Marcadet | 424/238 |
| 4,440,653 | 4/1984 | Briscoe et al. | 252/8.55 R |
| 4,464,293 | 8/1984 | Dobrin | 252/547 |
| 4,511,486 | 4/1985 | Shah | 252/90 |
| 4,574,052 | 3/1986 | Gupte et al. | 252/90 |
| 4,627,973 | 12/1986 | Moran et al. | 424/47 |
| 4,661,340 | 4/1987 | Nagy nee Kricsfalussy et al. | 424/47 |
| 4,673,569 | 6/1987 | Shernov et al. | 424/47 |
| 4,683,004 | 7/1987 | Goddard | 106/170 |
| 4,708,813 | 11/1987 | Snyder | 252/90 |
| 4,761,273 | 8/1988 | Grollier et al. | 424/47 |
| 4,798,722 | 1/1989 | Edman | 424/71 |
| 4,806,262 | 2/1989 | Snyder | 252/90 |
| 4,808,388 | 2/1989 | Beutler et al. | 424/47 |
| 4,956,170 | 9/1990 | Lee | 514/873 |
| 4,981,677 | 1/1991 | Thau | 424/45 |
| 5,002,680 | 3/1991 | Schmidt | 252/132 |

FOREIGN PATENT DOCUMENTS 1096753 12/1967 United Kingdom.

OTHER PUBLICATIONS

"The Chemical Formulary, vol. XVI", H. Bennett, Chemical Publishing Co., Inc., New York, N.Y., 1971, p. 109.

"The Chemical Formulary, vol. XX", H. Bennett, Chemical Publishing Co., Inc., New York, N.Y., 1977, p. 194.

"Aqueous Alcohol Aerosol Foams, Parts I & II", P. Sanders, Drug & Cosmetic Industry, Aug., 1966, p. 56ff and Sep., 1966, p. 57ff.

"A Formulary of Cosmetic Preparation", M. Ash et al., Chemical Publishing Co., New York, N.Y., 1977, pp. 98–100.

Primary Examiner—Thurman K. Page
Assistant Examiner—William E. Benston, Jr.

[57] ABSTRACT

This invention relates to a high alcohol content aerosol antimicrobial mousse which is dispensed as a foam for use as an antiseptic. The mousse composition comprises (1) 85–98% of an intermediate concentrate and (2) 2–15% of a hydrocarbon propellant. The intermediate concentrate comprises from 52–75% by weight of ethanol or isopropyl alcohol; from 0.1% to 1.5% by weight of a water-dispersible polymeric gelling agent; an amphiphilic system consisting of from 0.5% to 5.0% by weight of (a) at least one alcohol with a hydrocarbon group of from 16 to 22 carbons and (b) at least one nonionic surfactant, the hydrophilic balance (HLB) of the combination components "a" and "b" is in the range of 4.5 to 8.0 and the balance being at least 20 wt % of water. The hydrocarbon propellant is a saturated aliphatic hydrocarbon having from 2 to 6 carbon atoms.

23 Claims, No Drawings

HIGH ALCOHOL CONTENT AEROSOL ANTIMICROBIAL MOUSSE

Technical Field

The invention relates to an aerosol antimicrobial mousse-producing composition with a high level of alcohol as an active ingredient. The composition delivers a stable, disinfecting foam which breaks on pressure application to provide a creamy film of an alcoholic disinfectant.

BACKGROUND ART

It is well known that compositions containing at least 52% by weight of ethanol or isopropyl alcohol are antibacterial and, thus, widely accepted for disinfecting purposes.

Compositions with high alcohol content for disinfecting the hands are available as an antimicrobial alcoholic gel as described in U.S. Pat. No. 4,956,170 to Lee. While using gels to deliver an alcoholic disinfectant is satisfactory for many purposes, nonetheless, where patients have suffered burns or where skin conditions do not permit the spreading of a gel over an area to be treated, there exists a need for an alternate delivery system. That delivery system must be capable of providing disinfectant over an irritated or sensitive area without the pressure required to spread a gel.

In U.S. Pat. No. 2,054,989 to Moore, a semi-solid mass contains alcohol applied to the skin by massaging. The gelling agent used to make the alcohol mass semi-solid may be a soap and a wax. In this semi-solid form the alcoholic composition is dispersed on the skin by rubbing. However, the composition is unsuitable for application to highly sensitive skin.

Alcohol containing moisturizing products dispensed as foams are known, as disclosed in Bennett's *The Chemical Formulary*, Volume XVI, page 109 (1971), wherein a formulation of a "Fluff-Type Aerosol Moisturizing Cologne" containing 46% alcohol and having a fluorocarbon propellant is recited. The formulation for a Foam-Moisturizing product in *The Chemical Formulary*, Volume XX, page 194 (1977), includes 35% alcohol, 40% of a 1% solution of Carbopol ®941 (as a thickener) neutralized by diisopropanolamine, and a fluorocarbon propellant. Such alcoholic foaming formulations, however, have concentrations of alcohol lower than the 52% concentration normally required for suitable antimicrobial activity. Additionally, use of fluorocarbon propellants is undesirable for the deleterious effect on the environment and the solubility problems they present.

Mousse-forming compositions can be employed to cleanse skin as taught in U.S. Pat. No. 4,806,262 to Snyder. However, such preparations do not possess the high alcohol content required for antibacterial effect. The alcohol employed in amounts to 5% is used as an emollient and a mousse stabilizer. The propellants used in Snyder, nitrous oxide, carbon dioxide and nitrogen do not form a stable foam in the inventive compositions.

As employed herein the term "mousse" includes a composition which is dispensed as a foam and which remains in that form until mechanically compressed as by rubbing or touching. It is, therefore, necessary to provide a stable foam which will not collapse until subjected to the pressure of a mechanical action. However, the presence of alcohols in high concentration, until now, has often caused foams to collapse.

As noted in U.S. Pat. No. 3,131,153 to Klausner, the use of decreasing amounts of alcohol favors the formation of more stable foams. Klausner in Col. 2, lines 42–45, states that by using decreased amounts of alcohol more stable foams are formed. It is said that if more than 64% alcohol is used, then nonhomogeneous compositions are obtained.

U.S. Pat. No. 3,131,152 to Klausner is referred to in a two-part set of articles by Paul Sanders entitled "Aqueous Alcohol Aerosol Foams." The articles appeared in the Aug. 1966 (pp. 56 ff.) and September 1966 (pp. 57 ff.) *Drug and Cosmetic Industry*. At page 175 of the Sept. 1966 publication, several formulations from the '152 Klausner patent are recited. Among the compositions listed were an aerosol men's cologne foam containing 53% by weight ethanol and an aerosol rubbing compound containing 59.1% by weight ethanol. The propellants used by Sanders were preferred to be chlorofluorocarbons, although aliphatic hydrocarbons are also disclosed. The solubility characteristics of the chlorofluorocarbons differ from the hydrocarbon propellant used in the present invention. Thus, when using chloroflurocarbons, there is a problem of the incomplete solubility of the combination of surfactants in the aerosol. That results in the possibility of valve clogging and the formation of unstable foams. Further, the '152 Klausner patent does not teach use of a polymeric gelling agent or an amphiphilic nonionic stabilizer with a specific HLB.

A readily-collapsible, antiperspirant sprayable foam composition is taught in U.S. Pat. No. 3,395,214 to Mummert. The composition has 20–60% alcohol and 10–70% water. Cetyl alcohol is employed and an ethoxylated stearyl alcohol is used together with a thickener and antiperspirant. Freon, propane or isobutane were employed as the propellants. However, the surfactants employed in Mummert are not completely soluble with hydrocarbon propellants which results in precipitation thereof and clogged valves when the foam is dispensed.

The Mummert foams also disappear within a few seconds after dispensing and before any mechanical working of the dispensed material. The thickener employed in Mummert was a magnesium aluminum silicate ("Veegum"). It is believed that the undesired "Veegum" together with the surfactant used renders the compositions too unstable and unduly insoluble in the aerosol form.

U.S. Pat. No. 476,273 to Grollier et al. teaches an unstable aerosol foam containing cationic and/or anionic polymers that produce a foam in an aqueous solution. The alcohol content ($C_{1-8}$ alcohol) is said not to be more than 50%.

U.K. Pat. No. 1,096,753 to Yardley & Co. Ltd. (equivalent to U.S. Pat. No. 3,824,303) relates to a collapsible foam pre-electric shave lotion. The foam is formed from a 55–70% water:alcohol solution which contains 0.5 to 5% of a surfactant mixture which is an ester or ether of a higher monohydric or dihydric alcohol having eight or more carbon atoms and a higher alcohol. Hydrocarbon propellants can be used. However, the composition does not form a stable foam, lacks a polymeric gelling agent and does not teach the HLB balance of the present invention.

U.S. Pat. No. 4,627,973 to Moran et al. relates to an aerosol skin mousse containing a combination of moisturizers. The alcohol content is only 15–30% by weight.

U.S. Pat. No. 3,770,648 to Mackles is directed to an anhydrous aerosol foam. Mackles Example I4 relates to a hair cleaning foam containing 45% ethanol and only 5% water. A silicone resin is the foaming agent and a fluorocarbon propellant is used. Examples 16 and 17 disclose anhydrous antiperspirant foams containing 74% and 81% alcohol respectively. A silicone resin is the foaming agent and a fluorocarbon propellant is employed.

U.S. Pat. No. 4,440,653 to Briscoe et al. teaches a stable alcoholic foam to be used as a carrier fluid such as a treating fluid for subterranean oil wells. The composition contains a liquid phase of 50–100% alcohol, which may optionally contain water. A nonionic surfactant and thickening agent, such as guar gum, are combined in the alcoholic solution. The liquid is foamed with a gas or mixture of gases such as air, carbon dioxide or preferably nitrogen. The foam-forming gases used in Briscoe are not hydrocarbon propellants. Briscoe fails to employ an amphiphilic nonionic stabilizer or a higher alcohol and a polyethoxylated fatty alcohol. The foam merely functions to stimulate recovery of hydrocarbons (oil) in subterranean formations.

U.S. Pat. No. 4,511,486 to Shah teaches cleaning dentures with an aerated foam. The foamable liquid cleanser includes 1–10% surfactant, 0.1–10% humectant, 25–60% water and 35–70% ethanol or isopropyl alcohol. The foam is non-pressurized. In use the cleaner is forced into an air-mixer to form a foam.

U.S. Pat. No. 4,808,388 to Beutler et al. relates to a foamable cream for the skin which may be in the form of a mousse. Beutler teaches a creamy, oil-in-water emulsion using nitrous oxide or carbon dioxide as the propellant. Alcohols of long-chain fatty acids in concentrations of 0.5–4.5% are employed, but no ethanol or isopropanol is used.

U.S. Pat. No. 4,673,569 to Shernov et al. is directed to a mousse aerosol hair composition having water and alcohol phases. The alcohol phase includes 0.5% to 20% of an alcohol, such as ethanol, as a secondary solvent. The alcohol phase further contains a long-chain nonionic ester and a foam-forming agent. The water phase contains water, a film-forming resin and a corrosion inhibitor. The mousse composition also contains ammonium hydroxide with isobutane as the propellant.

U.S. Pat. No. 3,840,465 to Knowles et al. discloses a foam-producing composition including an aqueous solution of a foam-producing surfactant containing a propellant dispersed therein. The composition further includes a water-insoluble surfactant which is soluble in the propellant. The foam-producing surfactant is a fatty acid salt or synthetic surfactant and the propellant-soluble surfactant is an ethoxylated compound. The composition provides a very persistent foam which is said to last from 40 to 240 minutes. There is no disclosure of high amounts of alcohol being present nor of the collapse of the foam upon being subjected to pressure.

SUMMARY DISCLOSURE OF THE INVENTION

It is an object of the present invention to provide an alcoholic, disinfecting antimicrobial mousse product, which is readily spread over a subject. It is another object to provide an antimicrobial, alcoholic mousse which does not employ fluorocarbon propellants and is able to provide a stable, creamy foam which is an effective disinfectant upon application.

These and other objects and advantages will be apparent from the following description of the invention.

All weights provided herein are based on the total weight of the intermediate concentrate unless otherwise indicated.

This invention encompasses a high alcohol content aerosol antimicrobial mousse composition which includes (I) an intermediate concentrate in amounts from about 85% to 98% of the total weight of the mousse composition and (II) a propellant in amounts from about 2% to 15% of the total weight of the mousse composition. The intermediate concentrate includes from about 52% to 75% by weight of ethanol, isopropanol or mixtures thereof; from about 0.1 to 1.5% by weight of a water-dispersible polymeric gelling agent; from about 1.0% to 15% by weight of an amphiphilic nonionic stabilizer comprising (a) from about 0.5 to 5.0% by weight of at least one alcohol of the formula ROH, wherein R is a hydrocarbon group having from 16 to 22 carbon atoms and (b) from about 0.5% to 10% by weight of at least one nonionic surfactant of the formula $R'O(CH_2CH_2O)_xH$ where $R'$ is a hydrocarbon group having from 16 to 22 carbon atoms and x has an average value of 1 to 21, wherein the hydrophilic and lipophilic balance (HLB) of the combination of (a) and (b) is from about 4.5 to 8.0; and the balance being at least about 20% by weight of water.

The propellant is at least one saturated aliphatic hydrocarbon having from 2 to 6 carbon atoms per molecule. The propellant generally has a vapor pressure of about 17 to 108 pounds per square inch (0.12 to 0.74 MegaPascal - "MPa") gauge at 25° C.

The mousse delivery form is superior to a gel delivery form for sensitive skin because the alcohol disinfectant remains stabilized in the dispensed mousse foam for a longer period. The gel, on the other hand, is applied to a small area of the skin and then spread in expanding circles. Since the alcohol tends to evaporate from the gel almost immediately, there is little alcohol left at the edges of the expanding circles. However, when the mousse foam is applied, the alcohol remains stabilized in the mousse for a longer period of time.

BEST MODE FOR CARRYING OUT THE INVENTION

In a preferred embodiment the invention is directed to a high alcohol content mousse adapted for disinfectant and hospital uses. It is recognized by the Food and Drug Administration that a composition having a minimum of about 54% by weight of ethanol is considered to be antimicrobial because it is capable of killing gram positive and gram negative bacteria upon contact. The mousse form of the composition stabilizes the alcohol against immediate evaporation. When a measured amount of the mousse composition is applied to skin previously contaminated with bacteria, the bacterial colony count is typically reduced by a factor on the order of 10,000 times.

The mousse composition of the invention includes an intermediate concentrate of active ingredients and a hydrocarbon propellant for the intermediate concentrate. The intermediate concentrate includes an alcohol, a gelling agent, an amphiphilic nonionic stabilizer, and an aqueous carrier.

The antimicrobial effect of the present invention is best evidenced in the presence of about 52% to 75% by weight of an alcohol, preferably ethanol or isopropyl alcohol, or mixtures thereof. The alcohol may be either pure alcohol or denatured alcohol. A more preferred alcohol is ethanol and, most preferably, a denatured alcohol, Specially Denatured (SD) Alcohol 40-A. SD Alcohol 40-A is anhydrous alcohol which is denatured with t-butyl alcohol and sucrose octaacetate.

In order to provide a stabilized foam (mousse), the intermediate concentrate should contain a gelling agent (or thickening agent). The gelling agent preferably employed is a water-dispersible polymeric gelling agent. A more preferred gelling agent is an addition polymer of acrylic acid crosslinked with an unsaturated polyfunctional agent, such as polyalkyl ether of sucrose. The gelling agent assists in stabilizing the formulation to avoid early crystallization prior to filling in the dispenser. The intermediate concentrate is made thicker by the gelling agent for better mixing with the propellant to thus produce a more stable foam.

Preferred polymeric gelling agents are described in U.S. Pat. Nos. 2,798,053, 3,,133,865 and 4,956,170, the disclosures of which are incorporated by reference. They are also to be found listed in the CTFA (Cosmetic, Toiletry, and Fragrance Association), 3rd Edition, 1982, under the adoptive name "Carbomer." They are commercially available under the tradenames CARBOPOL® 934, 940, 941, 951 from B.F. Goodrich Chemicals Group of Cleveland, Ohio. Carbomer 951 is a more preferred gelling agent. Carbomer 951 is the same product as Carbomer 941, except that it is prepared in a benzene-free system, since the solvent used in its production is ethyl acetate.

Effective gelling agents are also available under the trade names ACRITAMER 934, 940 and 941 from R.I.T.A. Corporation of Crystal Lake, Illinois. Other thickening polymers and gums may be used according to their compatibility with the hydroalcoholic system. Other such suitable gelling agents include cellulosic ether polymers sold by Dow Chemical as Methocel® and hydroxymethyl, hydroxyethyl and hydroxypropyl cellulose gums sold under the mark Aqualon®.

Since the gelling ability of the preferred acrylic polymer thickeners is affected by the high alcohol content of the concentrate, it is best to maintain their gelling capability by neutralizing them. Accordingly, optimum thickening results are attained when the carboxyl groups present in the acrylic acid polymers are neutralized employing a suitable neutralizing agent sufficient to render the polymers more water soluble. Usually, from about 15 to 100% of the carboxyl groups present in the acrylic acid polymer are neutralized. Preferably at least about 50% of the carboxyl groups are neutralized.

Appropriate neutralizing agents include triethanolamine, sodium hydroxide, monoethanolamine and dimethyl stearylamine. Other neutralizing agents may be used, such as $HO(C_mH_{2m})_2NH$ where m has the value of from 2 to 3 and aminomethyl propanol, aminomethyl propanediol, and ethoxylated amines, i.e., $H(OCH_2CH_2)xRN(CH_2CH_2O)yH$, where R is a hydrocarbon radical having from 10 to 18 carbon atoms and the sum of $x+y$ has an average value of from about 5 to 25. An example of a suitable ethoxylated amine is PEG-25 cocamine (hydrocarbon groups are derived from coconut fatty acid and the sum of $x+y$ is 25). Other examples of suitable ethoxylated amines are polyoxyethylene (5) cocamine ("PEG-5 cocamine"); polyoxyethylene (25) cocamine ("PEG-25 cocamine"); polyoxyethylene (5) octadecylamine ("PEG-5 stearamine"); polyoxyethylene (25) octadecylamine ("PEG-25 stearamine"); polyoxyethylene (5) tallowamine ("PEG-5 tallowamine"); polyoxyethylene (15) oleylamine ("PEG-15 oleylamine"); polyethylene (5) soyamine ("PEG-5 soyamine"); and polyoxyethylene (25) soyamine ("PEG-15) soyamine"). A number of these are commercially available under the tradename of ETHOMEEN from Akzo Chemie America, Armak Chemicals of Chicago, Illinois.

The preferred neutralizing agent is triethanolamine (TEA).

The polymeric gelling agent is employed in amounts sufficient to provide the intermediate concentrate with sufficient viscosity, to render it pourable and to form a stabilized foam with the propellants. For this and other purposes from about 0.1 to 1.5% by weight of the water-dispersible polymeric gelling agent is employed. More preferably from about 0.1 to 0.8% by weight is employed.

The mousse composition is generally formulated as an emulsion having a water-alcohol phase, which includes the active ingredients. It is believed that a small portion of the hydrocarbon propellant is also solubilized in the water-alcohol phase. The balance of the propellant forms a separate layer. Upon discharge, the propellant solubilized in the water-alcohol phase expands and generates the stable aerosol mousse. For that and other purposes, it is necessary to formulate the mousse composition as a stable emulsion. The amphiphilic system of a long-chain alcohol and a nonionic surfactant, properly HLB balanced, acts to overcome the problem of phase separation when using hydrocarbon propellants and permits the intermediate concentrate to retain sufficient propellant to produce a stable foam upon discharge. In addition, the amphiphilic stabilizer remains stable upon pressurization with propellant and resists the tendency to desolubilize and to release components which could clog the aerosol valve.

The foam viscosity of the mousse foam is an indicator of the stability of the dispensed mousse. The foam viscosity at room temperature (20°–22° C.) should be from 2,000 to 40,000 centipoise —"cps" (2 to 40 pascal seconds —"Pa.s"), preferably from 15,000 to 30,000 cps (15 to 30 Pa.s), as measured by a Brookfield Heliopath digital LVTD Viscosimeter with a T-bar spindle at 12 rpm.

An important feature of the present invention is the presence of a mixture of a relatively long-chain alcohol and at least one nonionic surfactant to form an amphiphilic nonionic stabilizer system. The amphiphilic nonionic stabilizer system provides stable compositions when using the hydrocarbon propellants. The nonionic stabilizers employed are selected so as to have a hydrophile-lipophile balance (HLB) between 4.5 to 8. The HLB between the long-chain alcohol and the nonionic surfactant must be within the range of 4.5 to 8 so as to prevent the water-alcohol actives from desolubilizing and permitting solid precipitants or agglomerates to clog the orifice of the spray container.

In general, the test results have shown that when the HLB of the long-chain alcohol and nonionic emulsifier is between about 4.5 and 8, then the intermediate concentrate is translucent and generally homogeneous. The resulting foam is creamy and exhibits a satisfactory foam viscosity. For example, when the HLB is adjusted to 7.5, a very creamy stable foam with a foam viscosity on the order of 31,000 cps (31 Pa.s) may be obtained. When the HLB value was below about 4.5, then excessively creamy foams were produced which exhibited a reduced foam viscosity. Samples with an HLB value of 4.9 exhibited a creamy foam and yielded generally a viscosity reading of over 20,000 cps (20 Pa.s). Samples with HLB values of 9.7 provided oily or tacky foams with reduced viscosities on the order of 15,000 cps (15 Pa.s).

The long-chain alcohol of the amphiphilic stabilizer has the preferred formula ROH, wherein R is a hydrocarbon group of 16 to 22 carbon atoms. Typical alcohols include cetyl, stearyl, isostearyl, hydroxy stearyl, oleyl, ricinoleyl, behenyl, erucyl and 2-octadecenyl alcohols.

In general, the long-chain alcohol is employed in amounts sufficient to provide stabilizing effects. For this and other purposes, generally about 0.5 to 5% weight and, more preferably, 2.5% to 5.0% is used.

The nonionic surfactant preferably has the formula:

$$R'O(CH_2CH_2O)_xH$$

wherein R' is an aliphatic hydrocarbon group having 16-22 carbons and x has an average value from 1-21. Such surfactants are polyethoxylated fatty alcohols. The R'O-group can be derived from alcohols such as cetyl ($C_{16}$), stearyl ($C_{18}$), oleyl (C18), behenyl ($C_{20}$) and erucyl ($C_{22}$) alcohols. Lauryl alcohol, a $C_{12}$ alcohol and myristyl alcohol, a $C_{14}$ alcohol were unsatisfactory when employed as the fatty alcohol portion of the ethyloxylated fatty alcohol, since little or no foam was produced.

Typical preferred polyethoxylated fatty alcohols are the surfactants sold under the mark "BRIJ" by ICI Americas, Inc. Typical preferred polyethoxylated fatty alcohols include polyethoxylated stearyl alcohol containing an average of 21 moles of ethylene oxide or an average of 2 moles of ethylene oxide.

In general, sufficient amounts of polyethoxylated fatty alcohol are employed to provide a stable intermediate concentrate and a stable foam. For this and other purposes, from about 0.5-10% by weight is employed, more preferably 2.5% by weight.

In order to adjust the HLB within the desired range, more than one nonionic surfactant can be utilized. For example, a combination of polyethylated stearyl alcohol (2 moles ethylene oxide) at 1.875% by weight (HLB =4.9) and polyethoxylated stearyl alcohol (21 moles ethylene oxide) at 0.625% by weight (HLB =15.5) could be employed with cetearyl alcohol and ceteareth-20 (2.5% by weight) to provide an optimum HLB of about 6.75.

The combination of cetearyl alcohol and ceteareth-20 is available under the mark Ritapro 300 from R.I.T.A. Corp. in Crystal Lake, Illinois. Cetearyl alcohol is a combination of a cetyl and stearyl alcohol and ceteareth-20 is a mixture of cetyl ethers and stearyl ethers of polyethylene oxide having an average of about 20 oxide units.

Sufficient water, preferably deionized water, is used to form a stable intermediate concentrate. In general, at least about 20% by weight water is employed.

Compatible foam stabilizing and boosting surfactants can optionally be employed including lactic acid esters of monoglycerides sold under the mark "Lactodan" by Grinsted Products, Inc., of Industrial Airport, Kansas, as well as $R'CON(CH_2CH_2OH)yH_{2-y}$, where R' is an aliphatic hydrocarbon group of from 16 to 22 carbon atoms and y is 1 or 2. These surfactants include cationic emulsifiers, such as diquaternized tallow imidazoline methosulfate, sold as Sherex Varisoft 6112 (available from Sherex Chemical Co. Inc. in Dublin, Ohio); a triquaternized stearic phospholipid complex sold as Monaquat P-TS (available from Mono Industries, Inc., Patterson, New Jersey); hydroxystearamide propyltriamine salts, such as stearamide diethanolamine cyclamide, sold as Cas Chem Surfactols (available from Cyclo Chemicals Corp., Miami, Florida); lactic acid monoglycerides and food emulsifiers such as glyceryl monostearate, propylene glycol monostearate and sodium stearoyl lactylate.

A more preferred foam booster is a silicone wax or an encapsulated oil, such as stearoxytrimethylsilane and stearyl alcohol sold as Q5-0158A wax from Dow Corning and the 3M Microcapsule Mineral Oil.

Such foam stabilizers and boosters are preferably employed in amounts from about 0.1 to 10% by weight of the intermediate concentrate.

The hydrocarbon propellant employed is a saturated hydrocarbon or mixtures thereof. The hydrocarbon should have 2 to 6 carbon atoms and includes ethane, n-propane, n-butane, n-pentane, n-hexane, isopropane, isobutane and mixtures thereof.

The propellant should preferably exert a vapor pressure between about 17 and 108 pounds per square (0.12 to 0.74 MPa) inch gauge at 25° C. For this and other purposes the propellant is employed in amounts from about 2-15% by weight based on the total weight of the mousse composition, and preferably in amounts of about 10% to provide a preferred pressure of 52 p.s.i.g. (0.36 MPa).

Other typical ingredients which may be added to the mousse composition include fragrances, antimicrobial agents, skin protective agents, humectants, medicinal ingredients and other auxiliary materials which are conventionally used in cosmetic compositions.

It has been observed that very lipophilic substances, such as small amounts of silicone fluid, mineral oil, and esters, as, for example, isopropyl palmitate and isopropyl myristate, may disrupt foam stability because of the high solubilization of the main emulsifiers in the composition and should not be employed.

Glycerine, propylene glycol and urea are typical moisturizing agents (i.e., humectants) which may optionally be incorporated into the mousse Medicinal substances such as salicylic acid and boric acid may also be added to the system as well as topical anesthetics, such as lidocaine.

Additional antimicrobial agents, such as chlorhexidine digluconate, may also be added to enhance the antimicrobial properties of the antimicrobial mousse. Chlorhexidine digluconate is a preferred optional ingredient because it provides a long-term residual antimicrobial effect. It may be employed in amounts from about 0.1% to 8% by weight based on the intermediate concentrate.

The intermediate concentrate is employed in amounts from about 85-98% of the total mousse composition, although there may be circumstances which would permit more or less to be used. The intermediate concentrate may be prepared by admixing the ethanol, isopropanol or mixtures thereof with the gelling agent and stirring. Next, in sequence, the water, preferably deionized water, is added; the gelling agent is neutralized as required and the amphiphilic stabilizers are added with heating, if necessary. After cooling, optional volatile ingredients can be added. The intermediate concentrate is then pressurized with the propellant.

INDUSTRIAL APPLICABILITY

Compositions made in accordance with the above invention are employable in institutions such as hospitals, nursing homes and clinics or in the home where frequent contact with sources of bacteria and viruses are possible, and thus, a frequent need for degerming the hands arises. The user simply dispenses a golf ball size of the mousse into the palm and rubs the mousse over the hands until they are dry. The contact with the alcohol degerms the hands and if emollients and/or the humectants are employed, they can reduce the drying effects of the alcohol on the skin.

Typical ingredients employed in the mousse composition include:

Brij ®72—Steareth-2 (cetyl ether of polyethylene oxide having an average of about 2 ethylene oxide units) available from ICI Americas, Inc., Wilmington, Delaware.

Brij ®721—Steareth-21 (cetyl ether of polyethylene oxide having an average of about 21 ethylene oxide units) available from ICI America, Inc., Wilmington, Delaware.

Carbomer 95—an addition polymer of acrylic acid crosslinked with a polyallyl ether of sucrose available from B.F. Goodrich Chemicals Group, Cleveland, Ohio.

Cyclomide ®DS-280 - 1:1 Stearic diethanolamide from Alcolac, Inc.

Klucel ®—hydroxy propylcellulose available from Hercules, Inc., Wilmington, Delaware.

Lactodan ™ P 22—a lactic acid ester of a monoglyceride available from Grindsted.

Macol ® 261-115—a polyethylene glycol ether of stearyl alcohol available from Mazer Chemicals, Inc.

Monaquat ™ P-TS—a stearic-based triquaternary phospholipid complex available from Mona Industries Inc. in Patterson, New Jersey.

Myvatex ® Texture Lite Food Emulsifier - a combination of glyceryl monostearate, propylene glycol monostearate, and sodium stearoyl lactylate which is available from Eastman Chemical Products, Inc.

Polawax —a self emulsifying wax available from Croda, Inc.

Polawax A-31—composed of higher fatty alcohols such as cetyl and stearyl alcohol in combination with waxy ethylene oxide polymers and is available from Croda, Inc. of New York.

Q5-0158A —silicone wax and stearyl alcohol available from Dow Corning Corporation, Midland, Michigan.

Ritapro ®300 (RP-3021)—cetearyl alcohol and ceteareth-20 surfactant from R.I.T.A. Corporation, Crystal Lake, Illinois.

SD Alcohol 40A—anhydrous denatured alcohol.

Triethanolamine (TEA).

Varisoft ® 6112—tallow imidazoline methosulfate diquaternary available from Sherex Chemical Co. Inc. in Dublin, Ohio.

Veegum—a magnesium aluminum silicate which gels in water from R.T. Vanderbilt Co., Inc. of Norwalk, CT.

The following examples are set forth for the various preferred embodiments and are not limitative of scope. All parts and percentages are by weight unless otherwise indicated.

EXAMPLE 1

This Example illustrates the production of compositions of the present invention useful as antimicrobial mousse compositions. The ingredients for the composition in parts are as follows:

| Ingredients | Amount |
| --- | --- |
| S.D. Alcohol 40-A | 60.00 |
| Carbomer 951 | 0.20 |
| Deionized Water | 34.50 |
| TEA (85%) | 0.20 |
| Ritapro 300 | 5.00 |
| Fragrance | 0.10 |
| | 100.00 |

To prepare the mousse composition the Carbomer 951 was added to the alcohol at room temperature and stirred for five minutes. The deionized water was then added, and the mixture stirred for an additional five minutes. TEA was then added and the mixture again stirred for five minutes. The mixture was then heated to 120°–140° F. (48.9°–60° C.), and the Ritapro 300 was added and stirred until the entire amount was melted. After cooling down to 110°–100° F. (43.3°–37.8° C.), the fragrance was added. The density of the intermediate was found to be 0.842 g/ml.

Prior to pressurization of the intermediate, it was exposed to a vacuum of 13-15 p.s.i. (90–103 KiloPascal-"KPa"). The intermediate was maintained at 100° F (37.8° C.) and pressurized with the propellant, 10% of a combination of 30% isobutane and 70% propane (A-91 Propellant). A final pressure of 96 p.s.i. (0.64 MPa) was obtained and, after pressurization, the unit was well shaken.

The product yielded a creamy stable foam with the following foam density and foam viscosity:

(A) Foam density

The foam density measurement at room temperature (20°–22° C.) was made by transferring 40 ml of foam to a 40 ml container, care being taken to minimize air pockets during the filling of the container.

After 30 seconds, any excess sample was discarded, and the weight of the foam was determined. The foam density was then calculated to be 0.134 g/ml as follows:

$$\frac{5.37 \text{ g}}{40.0 \text{ ml}} = 0.134/\text{g ml or } 1.12 \text{ lbs/gallon}$$

(B) Foam Viscosity

The measurement was made by using a Brookfield Heliopath digital LVTD Viscosimeter. The T-bar spindle E was used at 12 rpm, and measurement was made at room temperature (20°–22° C.) after a period of one minute. The measured viscosity was 22,035 centipoise (22.035 Pa.s).

EXAMPLES 2-6

The following Examples were prepared in the same manner as in Example I except that the levels of Ritapro 300 were varied to determine their effect on foam viscosity.

| | Amount | | | | |
| --- | --- | --- | --- | --- | --- |
| Ingredients | Ex. 2 | Ex. 3 | Ex. 4 | Ex. 5 | Ex. 6 |
| S.D. Alcohol 40-A | 60.00 | 60.00 | 60.00 | 60.00 | 60.00 |
| Carbomer 951 | 0.20 | 0.20 | 0.20 | 0.20 | 0.20 |
| Deionized Water | 39.00 | 38.50 | 37.00 | 35.50 | 34.50 |
| TEA (85%) | 0.20 | 0.20 | 0.20 | 0.20 | 0.20 |
| Ritapro 300 | 0.50 | 1.00 | 2.50 | 4.00 | 5.00 |
| Fragrance | 0.10 | 0.10 | 0.10 | 0.10 | 0.10 |

-continued

| Ingredients | Ex. 2 | Ex. 3 | Ex. 4 | Ex. 5 | Ex. 6 |
|---|---|---|---|---|---|
| | 100.00 | 100.00 | 100.00 | 100.00 | 100.00 |

The measurements for foam density and foam viscosity for each sample were made as in Example 1.

| Example | Foam Density | Foam Viscosity | Foam Evaluation |
|---|---|---|---|
| 2 | 0.090 | 3081 cps (3.081 Pa.s) | Very wet and airy |
| 3 | 0.089 | 6047 cps (6.047 Pa.s) | Wet and creamy |
| 4 | 0.066 | 15210 cps (15.21 Pa.s) | Creamier and puffy |
| 5 | 0.055 | 21762 cps (21.762 Pa.s) | Soft and creamier |
| 6 | 0.053 | 29094 cps (29.094 Pa.s) | Creamier and stiff |

The measured foam viscosities were within the general desired range from 2,000 to 40,000 cps (2 to 40 Pa.s). The viscosity measurements and foam quality were more satisfactory when the concentration of Ritapro 300 was in the range of 4–5% weight.

COMPARATIVE EXAMPLES 1–8

The following Comparative Examples 1–8 (CE 1–8) were prepared to show the effect of employing lauryl alcohol, a $C_{12}$ alcohol (Comparative Examples 1–4) and myristyl alcohol, a $C_{14}$ alcohol (Comparative Examples 5–8) respectively, on foam viscosity. The amount of Ritapro 300 was reduced in proportion to the amount of lauryl (or myristyl) alcohol added. Formulations C. E. 1–8 were as follows:

| Ingredients | C.E. 1 | C.E. 2 | C.E. 3 | C.E. 4 |
|---|---|---|---|---|
| S.D. Alcohol 40-A | 60.00 | 60.00 | 60.00 | 60.00 |
| Carbomer 951 | 0.20 | 0.20 | 0.20 | 0.20 |
| Deionized Water | 34.50 | 34.50 | 34.50 | 34.50 |
| TEA (85%) | 0.20 | 0.20 | 0.20 | 0.20 |
| Ritapro 300 | 3.75 | 2.50 | 1.25 | — |
| Lauryl Alcohol | 1.25 | 2.50 | 3.75 | 5.00 |
| Fragrance | 0.10 | 0.10 | 0.10 | 0.10 |
| | 100.00 | 100.00 | 100.00 | 100.00 |

Comparative Examples 5–8 were prepared in the same manner, except for substituting myristyl alcohol for lauryl alcohol.

In the following Table 1, the measurements for foam density and foam viscosity were made as in Examples 1–6. As is apparent from the results, lauryl alcohol and myristyl alcohol cannot be used in the system of this invention as unsatisfactory foam or no foam at all was produced.

TABLE 1

| Example | Foam Density | Foam Viscosity | Foam Evaluation |
|---|---|---|---|
| CE 1 | 0.058 | 14820 cps (14.82 Pa.s) | unduly airy, slow-breaking foam |
| CE 2 | 0.044 | 10140 cps (10.14 Pa.s) | wet, very quick-breaking |
| CE 3 | 0 | 0 | no foam |
| CE 4 | 0 | 0 | no foam |
| CE 5 | 0.056 | 16770 cps (16.77 Pa.s) | large bubbles |
| CE 6 | 0.047 | 6240 cps (6.24 Pa.s) | runny, wet foam |
| CE 7 | 0 | 0 | no foam |
| CE 8 | 0 | 0 | no foam |

COMPARATIVE EXAMPLES 9–12

The following Examples were prepared according to the procedure in Example 1 to illustrate the effect of different hydrophilic-lipophilic balance (HLB) values obtained by varying the proportions of the surfactants Brij 72 and Brij 721 in combination with Ritapro 300 and using a propane propellant at high pressure.

| Ingredients | CE 9 | CE 10 | CE 11 | CE 12 | CE 13 |
|---|---|---|---|---|---|
| SD-Alcohol-40A | 60.00 | 60.00 | 60.00 | 60.00 | 60.00 |
| Carbomer 951 | 0.20 | 0.20 | 0.20 | 0.20 | 0.20 |
| Deionized Water | 34.50 | 34.50 | 34.50 | 34.50 | 34.50 |
| TEA (85%) | 0.20 | 0.20 | 0.20 | 0.20 | 0.20 |
| Ritapro 300 | 2.50 | 2.50 | 2.50 | 2.50 | 2.50 |
| Brij 72 | 2.50 | 1.875 | 1.25 | 0.625 | — |
| Brij 721 | — | 0.625 | 1.25 | 1.875 | 2.50 |
| Fragrance | 0.10 | 0.10 | 0.10 | 0.10 | 0.10 |
| | 100.00 | 100.00 | 100.00 | 100.00 | 100.00 |

The HLB and foam characteristics of the samples was as follows:

| Example | HLB | Foam Density | Foam Viscosity | Foam Evaluation |
|---|---|---|---|---|
| CE 9 | 4.9 | 0.063 | 43680 cps (43.68 Pa.s) | creamy |
| CE 10 | 7.5 | 0.084 | 45240 cps (45.24 Pa.s) | very creamy |
| CE 11 | 9.7 | 0.075 | 39000 cps (39 Pa.s) | glossy, creamy, tacky foam |
| CE 12 | 12.8 | 0.107 | 33540 cps (33.54 Pa.s) | airy, light foam |
| CE 13 | 13.5 | 0.05 | 23400 cps (23.4 Pa.s) | very quick-breaking, creamy foam |

Comparative Example 9 with an HLB of 4.9 provided creamy foam. At the HLB value of 7.5, a very cream, thick foam was obtained. The higher viscosity provided an extremely creamy foam which remained stable for a longer period of time, thereby increasing the availability of the alcohol due to slower evaporation of the alcohol. The comparative examples with an HLB of values of 9.7, 12.8 and 15.5 provided foams which were either too airy and light or broke too quickly before mechanical working. The purpose of the mousse composition of the present invention is to provide a stable foam which will not break before it is applied to the skin.

COMPARATIVE EXAMPLES 14 and 15

These comparative examples were prepared according to the procedure of Example 1.

| Ingredients | CE 14 | CE 15 |
|---|---|---|
| SD-Alcohol-40A | 60.00 | 60.00 |
| Carbomer 951 | 0.20 | 0.20 |

-continued

| Ingredients | Amount | |
|---|---|---|
| | CE 14 | CE 15 |
| Deionized Water | 34.50 | 34.50 |
| TEA (85%) | 0.20 | 0.20 |
| Ritapro 300 | 0.00 | 0.00 |
| Brij 72 | 5.00 | 0.00 |
| Brij 721 | 0.00 | 5.00 |
| Fragrance | 0.10 | 0.10 |
| | 100.00 | 100.00 |

In Comparative Examples 14 and 15, Ritapro 300 was omitted and the Brij 72 and/or Brij 721 was the only nonionic surfactant present. The HLB values for CE 14 and CE 15 were 4.9 and 15.5 respectively. The test results for the mousse compositions containing such surfactants were as follows:

| Example | HLB | Foam Density | Foam Viscosity | Foam Evaluation |
|---|---|---|---|---|
| CE 14 | 4.9 | 0.085 | 24180 cps (24.18 Pa.s) | unduly wet & glossy |
| CE 15 | 15.5 | 0.0 | 0.0 | no foam |

The results, when compared to Comparative Examples 9 and 13, show that the omission of Ritapro-300 results in an unsatisfactory foam system. This indicates that for optimum foam quality the HLB balance must be in the indicated range of from 4.5 to 8.0, and that a fatty alcohol (ROH) with 16-22 carbon atoms must be present.

EXAMPLE 7

The following Example was prepared according to the procedure in Example 1 to show use of a different mixture of hydrocarbons as the propellant.

| Ingredients | Amount |
|---|---|
| S.D. Alcohol 40-A | 60.00 |
| Carbomer 951 | 0.20 |
| Deionized Water | 34.50 |
| TEA (85%) | 0.20 |
| Ritapro 300 | 2.50 |
| Brij 72 | 1.875 |
| Brij 721 | 0.625 |
| Fragrance | 0.10 |
| | 100.00 |

Instead of the A-91 Propellant, a B-52 Propellant containing a ratio of 30/30/40 of propane/isobutane/n-butane was used. The foam measurements were made as in Example I with the following results:
Foam density—0.050 g/ml.
Foam Viscosity—30420 cps (30.42 Pa.s)
Foam evaluation—very creamy coated feel.

EXAMPLES 8-2

In the following Examples 8-12, chlorhexidine digluconate was employed as an antimicrobial agent which was added to extend the antimicrobial property of the mousse by providing a long-term residual killing effect. In place of Carbomer 951, which is an anionic water-dispersible polymeric gelling agent, a nonionic cellulosic thickener was used. That was deemed necessary since the chlorhexidine digluconate has a positive charge and may precipitate out the anionic agent. Varying amounts of the chlorhexidine digluconate were employed. The samples were prepared as in Example 7 using B-52 Propellant.

| Ingredients | Amount | | | | |
|---|---|---|---|---|---|
| | Ex. 8 | Ex. 9 | Ex. 10 | Ex. 11 | Ex. 12 |
| S.D. Alcohol 40-A | 60.00 | 60.00 | 60.00 | 60.00 | 60.00 |
| Klucel (hydroxy-propylcellulose) | 0.20 | 0.20 | 0.20 | 0.20 | 0.20 |
| Deionized Water | 14.62 | 19.68 | 24.71 | 29.76 | 32.23 |
| Ritapro 300 | 2.50 | 2.50 | 2.50 | 2.50 | 2.50 |
| Brij 72 | 1.875 | 1.875 | 1.875 | 1.875 | 1.875 |
| Brij 721 | 0.625 | 0.625 | 0.625 | 0.625 | 0.625 |
| Chlorhexidine digluconate (20%) | 20.18 | 15.12 | 10.09 | 5.04 | 2.57 |
| | 100.00 | 100.00 | 100.00 | 100.00 | 100.00 |

The samples were analyzed and the measurements were made as in Example 1.

| Example | Foam Density | Foam Viscosity | Foam Evaluation |
|---|---|---|---|
| 8 | 0.050 | 29920 cps (29.92 Pa.s) | creamy, stable |
| 9 | 0.049 | 30050 cps (30.05 Pa.s) | creamy, stable |
| 10 | 0.056 | 29850 cps (29.85 Pa.s) | creamy, stable |
| 11 | 0.048 | 28750 cps (28.75 Pa.s) | creamy, stable |
| 12 | 0.055 | 31200 cps (31.20 Pa.s) | creamy, stable |

The results illustrate that long term antimicrobial effects may be imparted to the mousse composition by the addition of an antimicrobial agent while maintaining the excellent foam characteristics.

EXAMPLE 13

The following example includes a silicone wax and a humectant.

| Ingredients | Amount |
|---|---|
| SD Alcohol 40-A | 60.00 |
| Carbomer 951 | 0.20 |
| Deionized Water | 30.50 |
| TEA (85%) | 0.20 |
| Ritapro 300 | 5.00 |
| Q5-0158A (silicone wax) | 1.00 |
| Fragrance | 0.10 |
| Glycerine (humectant) | 3.00 |
| | 100.00 |

The mousse compositions were prepared and the foam measurements were made as in Example 1.

| Foam Density | Foam Viscosity | Foam Evaluation |
|---|---|---|
| 0.053 | 31200 cps (31.20 Pa.s) | very creamy |

Q5-01584 is a foam booster which acts together with the Ritapro 300 to provide a very creamy foam.

EXAMPLES 14-18

The following formulations, prepared according to Example 1, illustrate additional examples of mousse compositions in which various cosmetic additives were also employed.

|  | Amount | | | | |
|---|---|---|---|---|---|
| Ingredients | Ex. 14 | Ex. 15 | Ex. 16 | Ex. 17 | Ex. 18 |
| SD Alcohol 40-A | 60.00 | 60.00 | 60.00 | 60.00 | 60.00 |
| Carbomer 951 | 0.20 | 0.20 | 0.20 | 0.20 | 0.20 |
| Deionized Water | 34.50 | 34.50 | 34.50 | 34.50 | 24.50 |
| TEA (85%) | 0.20 | 0.20 | 0.20 | 0.20 | 0.20 |
| Ritapro 300 | 2.50 | 3.75 | 3.75 | 3.75 | 5.00 |
| Myvatex Texture Lite | 2.50 | — | — | — | — |
| Lactodan P22 | — | 1.25 | — | — | — |
| Varisoft 6112 | — | — | 1.25 | — | — |
| Monaquat P-TS | — | — | — | 1.25 | — |
| Urea | — | — | — | — | 10.00 |
| Fragrance | 0.10 | 0.10 | 0.10 | 0.10 | 0.10 |
|  | 100.00 | 100.00 | 100.00 | 100.00 | 100.00 |

In Example 16, after the addition of the Varisoft 6112, a yellow precipitate was observed to form which remained in the viscous gel that formed.

| Example | Foam Density | Foam Viscosity | Foam Evaluation |
|---|---|---|---|
| 14 | 0.12 | 37440 cps (37.44 Pa.s) | creamy rich |
| 15 | 0.11 | 38610 cps (38.61 Pa.s) | creamy, soft |
| 16 | 0.06 | 17550 cps (17.55 Pa.s) | creamy foam with small texture; coated skin feel after washing |
| 17 | 0.07 | 19110 cps (19.11 Pa.s) | creamy foam; coated skin feel after washing |
| 18 | 0.05 | 31200 cps (31.20 Pa.s) | creamy foam; skin softening feel after application |

EXAMPLES 19–20

A formulation was prepared according to Example 1 to illustrate the use of a medicinal substance, such as salicylic acid and 2-phenoxyethanol, in the mousse compositions of the invention. The preparation in Example 19 was made and tested as in Example 1 while Example 20 was made as in Example 7. In each example, the ingredients were mixed together in the order listed.

|  | Amount | |
|---|---|---|
| Ingredients | Ex. 19 | Ex. 20 |
| SD-Alcohol-40A | 60.00 | 60.00 |
| Carbomer 951 | 0.20 | 0.20 |
| Deionized Water | 32.50 | 32.60 |
| TEA (85%) | 0.20 | 0.20 |
| Ritapro 300 | 5.00 | 2.50 |
| Salicylic acid | 2.00 | — |
| Fragrance | 0.10 | — |
| Brij 72 | — | 1.875 |
| Brij 721 | — | 0.625 |
| Q5-0184 (Silicone Wax) | — | 0.60 |
| Myvatex Texture Lite | — | 0.20 |
| Cyclomide DS-280 | — | 0.20 |
| 2-Phenoxyethanol | — | 1.00 |
|  | 100.00 | 100.00 |

| Example | Foam Density | Foam Viscosity | Foam Evaluation |
|---|---|---|---|
| 19 | 0.064 | 31980 cps (31.98 Pa.s) | creamy, rich texture; skin soft after application |
| 20 | 0.050 | 31200 cps (31.20 Pa.s) | creamy, oily |

EXAMPLES 21–23

The following samples were prepared according to Example 7 and were made to determine the effect on foam stability and quality at different levels of petrolatum and glycerine.

|  | Amount | | |
|---|---|---|---|
| Ingredients | Ex. 21 | Ex. 22 | Ex. 23 |
| SD Alcohol 40-A | 60.00 | 60.00 | 60.00 |
| Carbomer 951 | 0.20 | 0.20 | 0.20 |
| Deionized Water | 29.85 | 27.60 | 23.10 |
| Glycerine | 1.50 | 3.00 | 6.00 |
| TEA (85%) | 0.20 | 0.20 | 0.20 |
| Petrolatum | 0.75 | 1.50 | 3.00 |
| Ritapro 300 | 2.50 | 2.50 | 2.50 |
| Brij 72 | 1.875 | 1.875 | 1.875 |
| Brij 721 | 0.625 | 0.625 | 0.625 |
| Myvatex Texture Lite | 0.20 | 0.20 | 0.20 |
| Cyclomide DS-280 | 0.20 | 0.20 | 0.20 |
| Q5-0158A (Silicone Wax) | 1.00 | 1.00 | 1.00 |
| Macol 261-115 | 1.00 | 1.00 | 1.00 |
| Fragrance | 0.10 | 0.10 | 0.10 |
|  | 100.00 | 100.00 | 100.00 |

The test results for foam density and viscosity were as follows:

| Example | Foam Density | Foam Viscosity | Foam Evaluation |
|---|---|---|---|
| 21 | 0.0825 | 20670 cps (20.67 Pa.s) | creamy, soft feel |
| 22 | 0.0775 | 20670 cps (20.67 Pa.s) | creamy, soft feel |
| 23 | 0.0575 | 10920 cps (10.92 Pa.s) | creamy, soft feel |

The presence of the additional foam boosters and stabilizers Myvatex Texture Lite, Cyclomide DS-280 and Macol 261-115 prevents the petrolatum from interfering with foam stability and quality.

The following comparative tests were performed on comparative aerosol or mousse formulations prepared generally according to the formulas in British Patent 1,096,753, U.S. Pat. No. 3,131,852, U.S. Pat. No. 3,395,214 and in the Paul Sanders' article "Aqueous Alcohol Aerosol Foams" employing the procedures of Example 1.

COMPARATIVE EXAMPLE 15

A collapsible foam pre-electric shave lotion very similar to Example 1 in British Patent 1,096,753 to Yardley & Co., Ltd. was prepared as follows:

| Ingredients | Amount |
|---|---|
| Dimethyl esters of glutaric, adipic and succinic acids | 2.40 |
| Denatured ethyl alcohol (95%) | 68.10 |
| Polawax A-31 | 4.90 |
| Water | 21.90 |

-continued

| Ingredients | Amount |
|---|---|
| Isobutane (Propellant) | 2.70 |
| | 100.00 |

The Polawax A-31 was added to the ethyl alcohol at 110° F. (43.3° C.). Water and the mixture of dimethyl esters of glutaric, succinic and adipic acid was then added to form the intermediate. Dispensing units containing the intermediate were pressurized with the propellant.

The pressurized composition was tested for foam characteristics and the results were as follows:

| Foam Density | Foam Viscosity | Foam Evaluation |
|---|---|---|
| 0 | 0 | no foam formed |

COMPARATIVE EXAMPLE 16

A pressurized mousse formulation according to Example 6 of U.S. Pat. No. 3,131,152 to Klausner was prepared and tested according to Example 1.

| Intermediate Ingredients | Amount |
|---|---|
| Polawax | 1.5 |
| Anhydrous ethyl alcohol | 58.5 |
| Perfume | 2.0 |
| Water | 38.0 |
| | 100.0 |

The Polawax was dissolved in the ethyl alcohol at 110° F. (43.3° C.). The water and perfume were added while maintaining the same temperature. The units were pressurized with 97% intermediate and 3% of isobutane (A-31) propellant.

The product evaluation results were as follows:

| Foam Density | Foam Viscosity | Foam Evaluation |
|---|---|---|
| 0.142 | 2730 cps (2.73 Pa.s) | very runny |

COMPARATIVE EXAMPLE 17

The antiperspirant sprayable foam of U.S. Pat. No. 3,395,214, to Mummert described in the Example set forth in column 3 was prepared using the procedure of Example 1 as follows:

| Nonpressurized Intermediate | Amount |
|---|---|
| Cetyl alcohol | 1.0 |
| Polawax | 4.0 |
| 1% Veegum solution | 15.0 |
| Aluminum chlorohydroxide | 19.5 |
| Aluminum sulfate | 7.0 |
| Aluminum chlorohydroxy allantoinate | 0.5 |
| Ethanol | 39.9 |
| Fragrance | 0.1 |
| Water | 13.0 |

The cetyl alcohol, Polawax and 1% Veegum were added together and heated until all the Polawax was completely melted.

In a separate container the antiperspirant additives were added (aluminum chlorohydroxide in water and aluminum sulfate), heated to 70° C. and added to the Polawax mixture. The ethanol and fragrance were then added. At 50-60° C. the sample was pressurized with 10% by weight of isobutane propellant.

The composition formed was a two-phase system and insoluble materials were seen. No foam was produced and the valve clogged.

COMPARATIVE EXAMPLE 18

An aerosol men's cologne foam, Formula KCD-4424, from page 175 of "Aqueous Alcohol Aerosol Foams", Second Part, by Paul Sanders (noted earlier) was prepared as follows:

| Ingredients | Amount |
|---|---|
| Water | 33.0 |
| Anhydrous ethyl alcohol | 53.0 |
| Polawax | 2.0 |
| Perfume | 2.0 |
| Propellant* (30/30/40 propane/ isobutane/n-butane- B-52 Propellant) | 10.0 |
| | 100.0 |

*A hydrocarbon propellant was substituted for the Sanders Freon propellant.

The water, alcohol and Polawax were added to a container and heated to 120° F.-140° F. (48.9° C.-60° C.) until the Polawax completely melted. After the blend cooled down to 100° F.-110° F. (37.8° C.-43.3° C.), the fragrance was added. The intermediate was pressurized in a glass bottle.

The product evaluation results for foam characteristics were as follows:

| Foam Density | Foam Viscosity | Foam Evaluation |
|---|---|---|
| 0.05 | 1404 cps (1.404 Pa.s) | light, large bubbles, quick breaking |

COMPARATIVE EXAMPLE 19

Formulation KCD 4735 for an aerosol rubbing compound from "Aqueous Alcohol Aerosol Foams", Second Part, by Paul Sanders (noted above) was emulated as follows:

| Ingredients | Amount |
|---|---|
| Water | 27.8 |
| Anhydrous ethyl alcohol | 59.1 |
| Fragrance | 0.1 |
| Polawax | 3.0 |
| Propellant* (30/30/40 propane/ isobutane, n-butane- B-52 Propellant) | 10.0 |
| | 100.0 |

*A hydrocarbon propellant was used in place of the Freon propellant of Sanders and a fragrance was substituted for hexachlorophene.

The product evaluation results for foam characteristics were as follows:

| Foam Density | Foam Viscosity | Foam Evaluation |
|---|---|---|
| 0.055 | 780 cps | light, large bubbles, |

| Foam Density | Foam Viscosity | Foam Evaluation |
|---|---|---|
| | (0.78 Pa.s) | quick breaking |

EXAMPLE 20

The following test results illustrate the antibacterial effects of the inventive mousse compositions compared to commercial disinfectants and cleansers. In the tests fingernails were contaminated by *Serratia marcescens* and *Escherichia coli*, respectively. The below products were then applied to the contaminated fingernail regions. In Table 2 the column "Untreated" lists the log to the base 10 of the number of colonies of bacteria on the untreated skin. The figures listed are based on an average of 8 measurements. The first number listed for each product is for *S. Marcesens* and the second is for *E. coli*. The column "Treated" provides the number of colonies (log base 10) remaining after treatment with 2.5 ml of the applied products. The test results represent the average of 8 tests per product applied. The results indicate the number of bacterial colonies of *Serratia marcescens* and *Escherichia coli*, respectively, remaining after the application.

TABLE 2

| Product | Untreated | Treated | |
|---|---|---|---|
| Inventive High Alcohol | 7.12 | 3.30 | S. Marcescens |
| Content Mousse | 6.37 | 2.84 | E. coli |
| Alcohol Wipe | 7.35 | 6.31 | |
| | 6.65 | 5.70 | |
| DELIVER TM Alcohol | 7.35 | 4.08 | |
| Gel from S. C. Johnson & Son, Inc. | 6.65 | 3.19 | |
| Ultracol TM (bactericidal alcohol hand gel) from Dexide Corporation | 7.51 | 4.27 | |
| | 6.58 | 3.71 | |
| Calstat (bactericidal soap) from Calgon Corporation | 7.51 | 4.46 | |
| | 6.58 | 3.44 | |
| Ivory Liquid from Procter & Gamble | 7.24 | 5.98 | |
| | 6.68 | 4.26 | |
| Liquid Dial from The Dial Corporation | 7.24 | 6.62 | |
| | 6.68 | 5.44 | |

As can be seen from the above results the high alcohol content mousse of the invention reduced the bacterial colony count by a factor of almost $10^4$. The present mousse composition showed high efficiency in treating skin contaminated with bacteria and demonstrates the superior antimicrobial activity imparted by the mousse delivery system.

The invention is not to be limited except as set forth in the following claims.

What I claim is:

1. A high alcohol content aerosol antimicrobial mousse composition comprising:
   (I) an intermediate concentrate having
      (a) from about 52%-75% by weight of the intermediate concentrate of ethanol, isopropanol or mixtures thereof;
      (b) from about 0.1%-1.5% by weight of the intermediate concentrate of a water-dispersible polymeric gelling agent;
      (c) from about 1% to 15% by weight of the intermediate concentrate of an amphiphilic nonionic stabilizer consisting essentially of
         (i) from about 0.5%-5.0% of the intermediate concentrate of at least one alcohol of the formula ROH where R is a hydrocarbon group having from 16 to 22 carbons; and
         (ii) from about 0.5%-10% by weight of the intermediate concentrate of at least one nonionic surfactant of the formula $R'O(CH_2CH_2O)_xH$ were R' is a hydrocarbon group having from 16 to 22 carbon atoms and x has an average value of from 1 to 21; wherein the hydrophilic-lipophilic balance of the combination of (i) and (ii) is from about 4.5 to 8.0; and
      (d) the balance consisting essentially of water in an amount of at least about 20% by weight of the intermediate concentrate; and
   (II) a saturated aliphatic hydrocarbon propellant having from 2 to 6 carbon atoms;
   wherein the intermediate concentrate (I) is from about 85%-98% of the total aerosol mousse composition and the propellant (II) is from about 2%-15% of the total aerosol mousse composition.

2. The composition according to claim 1, wherein the intermediate concentrate further contains from about 0.1%-10% by weight of stearoxytrimethylsilane.

3. The composition according to claim 1, wherein the intermediate concentrate further contains from about 0.1% to 10% weight of a microencapsulated hydrocarbon oil.

4. The composition according to claim 1, wherein the intermediate concentrate further contains from about 0.1% to 10% by weight of a long-term antimicrobial agent.

5. The composition according to claim 1, wherein the intermediate concentrate further contains from about 0.1% to 10% by weight of a humectant.

6. The composition according to claim 5, wherein the humectant is selected from the group consisting of propylene glycol, glycerine and urea.

7. The composition according to claim 1, wherein the intermediate concentrate further contains from about 0.1% to 10% by weight of a cationic skin conditioning agent.

8. The composition according to claim 1, wherein the intermediate concentrate further contains a medicinal agent.

9. The composition according to claim 8, wherein the medicinal agent is a topical anesthetic.

10. The composition according to claim 8, wherein the medicinal agen tis an antiacne agent.

11. The composition according to claim 1, wherein the intermediate concentrate further contains a sunscreen.

12. The composition according to claim 1, wherein the intermediate concentrate contains an insect repellant.

13. The composition according to claim 1, wherein the alcohol is ethanol.

14. The composition of claim 1, wherein ROH is an alcohol selected from the group consisting of cetyl, stearyl, hydroxystearyl, oleyl, ricinoleyl, behenyl, and erucyl alcohol.

15. The composition of claim 1, wherein the gelling agent is an addition polymer of acrylic acid cross-linked with an unsaturated polyfunctional agent wherein from 15%-100% of acrylic acid carboxyl groups present are neutralized with a base.

16. The composition according to claim 15, wherein the unsaturated polyfunctional agent is a polyallyl ether of sucrose.

17. The composition according to claim 15, wherein the base is selected from an organic amine, sodium hydroxide or ammonium hydroxide.

18. The composition according to claim 17, wherein said base is triethanolamine.

19. The composition according to claim 1, including from about 0.1% to 10% by weight of the intermediate concentrate of at least one compatible foam stabilizing and boosting surfactant selected from the group consisting of lactic acid esters of monoglycerides, $R'CON(CH_2CH_2O)_yH_{2-y}$ where R' is an aliphatic hydrocarbon group of from 16 to 22 carbon atoms and y is 1 or 2, a diquaternized tallow imidazoline stearic phospholipid complex, a hydroxystearamide propyltriamine salt, glyceryl monostearate, propylene glycol monostearate and sodium stearoyl lactate.

20. The composition according to claim 19, wherein the surfactant is stearic acid monoesterified with a moiety selected from the group consisting of propylene glycol and glycerine, sodium stearoyl lactylate, and $R'CON(CH_2CH_2OH)_yH_{2-y}$ where y is 1 or 2.

21. The composition according to claim 1, wherein the propellant is selected from the group consisting of ethane, n-propane, n-butane, n-pentane, n-hexane, isobutane and isopropane.

22. The composition according to claim 1, wherein the propellant has a vapor pressure of about 17-108 pounds per square inch (0.12-0.74 Mega Pascal) gauge at 25° C.

23. A high alcohol content aerosol antimicrobial mousse composition comprising:

(I) an intermediate concentrate having (a) from about 52%-75% by weight of the intermediate concentrate of ethanol, isopropanol or mixtures thereof;
(b) from about 0.1%-1.5% by weight of the intermediate concentrate of a water-dispersible polymeric gelling agent;
(c) from about 1% to 15% by weight of the intermediate concentrate of an amphiphilic nonionic stabilizer consisting essentially of
  (i) from about 0.5%-5.0% of the intermediate concentrate of at least one alcohol of the formula ROH where R is a hydrocarbon group having from 16 to 22 carbons; and
  (ii) from about 0.5%-10% by weight of the intermediate concentrate of at least one nonionic surfactant of the formula $R'O(CH_2CH_2O)_xH$ where R' is a hydrocarbon group having from 16 to 22 carbon atoms and x has an average value of from 1 to 21; wherein the hydrophilic-lipophilic balance of the combination of (i) and (ii) is from about 4.5 to 8.0;
(d) from about 0.1% to 10% by weight of a cationic skin conditioning agent selected from the group consisting of a diquaternized tallow imidazoline methosulfate, a triquaternized stearic-phospholipid complex and a hydroxy stearamide propyltriammonium salt; and
(e) the balance consisting essentially of water in an amount at least about 20% by weight of the intermediate concentrate; and wherein the intermediate concentrate (I) is from about 85%-98% of the total aerosol mousse composition and the propellant (II) is from abut 2%-15% of the total aerosol mousse composition.

* * * * *

UNITED STATES PATENT AND TRADEMARK OFFICE
CERTIFICATE OF CORRECTION

PATENT NO. : 5,167,950

DATED : December 1, 1992

INVENTOR(S) : Claudio L. K. Lins

It is certified that error appears in the above-identified patent and that said Letters Patent is hereby corrected as shown below:

In column 22, line 31, the phrase -- (II) a saturated aliphatic hydrocarbon propellant having from 2 to 6 carbon atoms; -- should be added.

Signed and Sealed this

Twenty-sixth Day of October, 1993

Attest:

BRUCE LEHMAN

*Attesting Officer*   *Commissioner of Patents and Trademarks*